(12) United States Patent
Turner

(10) Patent No.: US 6,875,233 B1
(45) Date of Patent: Apr. 5, 2005

(54) HINGING BREAST IMPLANT

(76) Inventor: Matthew Lamar Turner, P.O. Box 3052, Gainesville, GA (US) 30503

( * ) Notice: Subject to any disclaimer, the term of this patent is extended or adjusted under 35 U.S.C. 154(b) by 0 days.

(21) Appl. No.: 10/457,969

(22) Filed: Jun. 10, 2003

(51) Int. Cl.[7] .............................................. A61F 2/12
(52) U.S. Cl. ....................................................... 623/8
(58) Field of Search .......................... 623/7–8; 450/39, 450/54, 55

(56) References Cited

U.S. PATENT DOCUMENTS

| | | | |
|---|---|---|---|
| 3,559,214 A | | 2/1971 | Pangman |
| 3,641,592 A | * | 2/1972 | Den Bleyker ................... 623/7 |
| 3,683,424 A | | 8/1972 | Pangman |
| 3,845,507 A | * | 11/1974 | Kirby et al. .................... 623/7 |
| 4,433,440 A | * | 2/1984 | Cohen ............................ 623/8 |
| 4,605,412 A | | 8/1986 | LaForest et al. |
| 4,790,848 A | | 12/1988 | Cronin |
| 4,841,992 A | | 6/1989 | Sasaki et al. |
| 4,955,907 A | | 9/1990 | Ledergerber |
| 5,071,433 A | * | 12/1991 | Naestoft et al. ............... 623/7 |
| 5,092,882 A | | 3/1992 | Lynn et al. |
| 5,133,752 A | | 7/1992 | Mandelkern |
| 5,147,398 A | | 9/1992 | Lynn et al. |
| 5,236,454 A | | 8/1993 | Miller |
| 5,383,929 A | | 1/1995 | Ledergerber |
| 5,496,367 A | | 3/1996 | Fisher |
| 5,571,179 A | | 11/1996 | Manders et al. |
| 5,759,204 A | | 6/1998 | Seare, Jr. |
| 5,779,734 A | | 7/1998 | Ledergerber |
| 5,961,552 A | | 10/1999 | Iversen et al. |
| 6,113,634 A | * | 9/2000 | Weber-Unger et al. ........ 526/7 |
| 6,146,418 A | * | 11/2000 | Berman ......................... 623/8 |
| 6,187,043 B1 | * | 2/2001 | Ledergerber .................... 623/8 |
| 6,228,116 B1 | * | 5/2001 | Ledergerber .................... 623/8 |
| 2001/0010024 A1 | | 7/2001 | Ledergerber |
| 2002/0038147 A1 | * | 3/2002 | Miller, III ..................... 623/8 |
| 2002/0193878 A1 | * | 12/2002 | Bowman et al. ............... 623/7 |
| 2003/0105523 A1 | * | 6/2003 | Weber-Unger et al. ........ 623/7 |

FOREIGN PATENT DOCUMENTS

DE          199 17 032 A1  *  4/1999

* cited by examiner

Primary Examiner—David H. Willse
Assistant Examiner—Suzette J. Jackson
(74) Attorney, Agent, or Firm—Hinkle + O'Bradovich, LLC

(57) ABSTRACT

A hinging breast implant capable a being variably sized and that includes an exterior shell and an inner bladder is described. The exterior shell is typically a bellows having a plurality of pleats so that the outer size of the implant is variable so that different sizes and shapes can be obtained. The rear of the housing closest to the patient's interior is typically shaped in order to conform to the patient's rib cage and internal connective tissues. Conversely, the front of the housing is shaped to naturally conform to the outer shape of the patient. The inner bladder can be filled with a suitable filling material, liquid, gas or solid. As the bladder is filled, the exterior shell expands in a manner that creates a lifting effect and a ballooning effect. An appendage, used to fill the bladder external to the patient, is connected to both the exterior shell and the inner bladder.

13 Claims, 2 Drawing Sheets

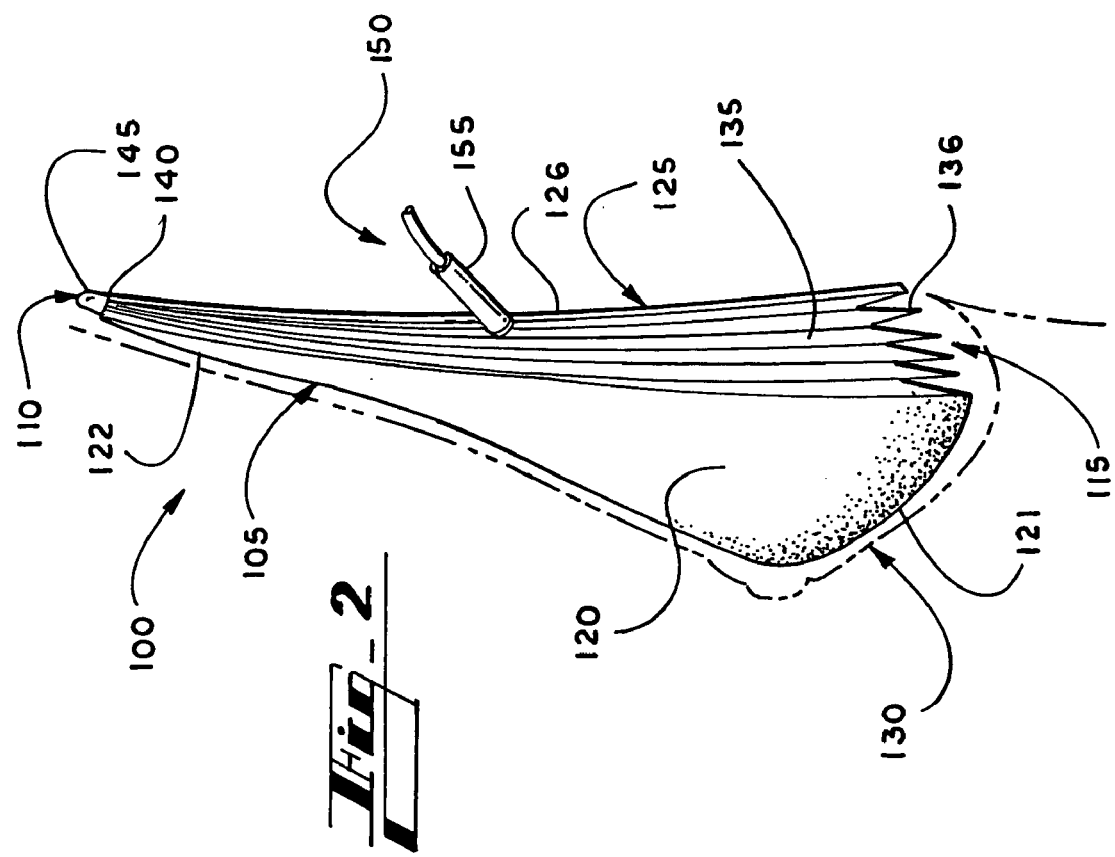
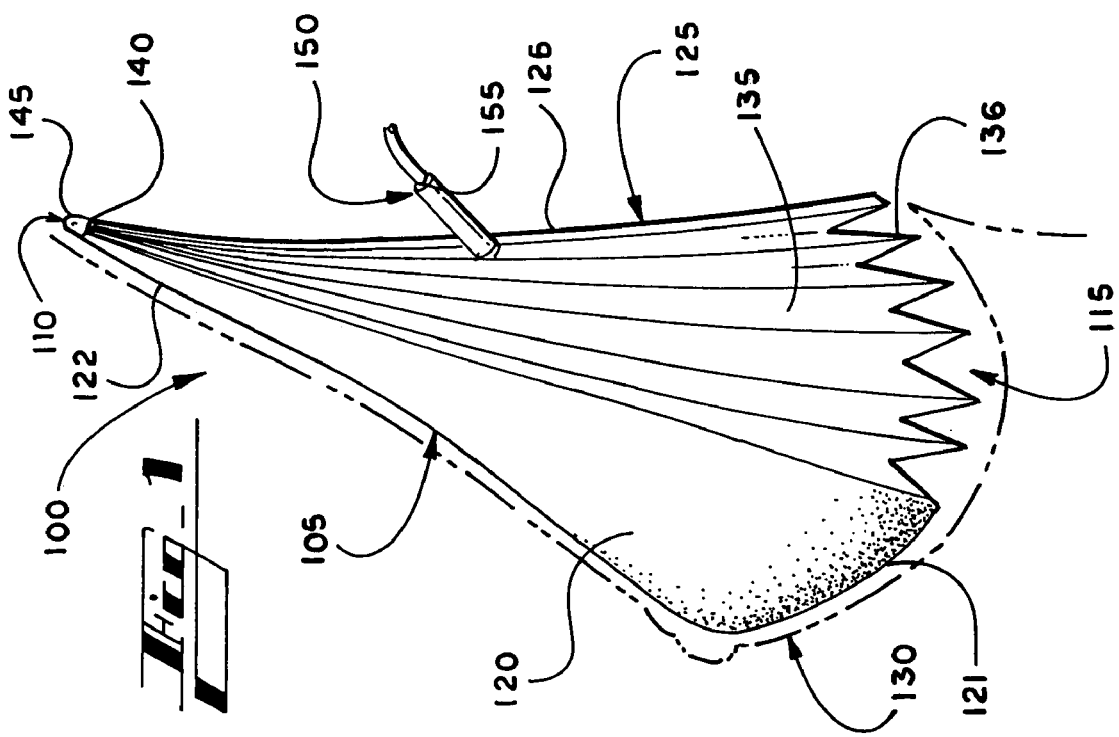

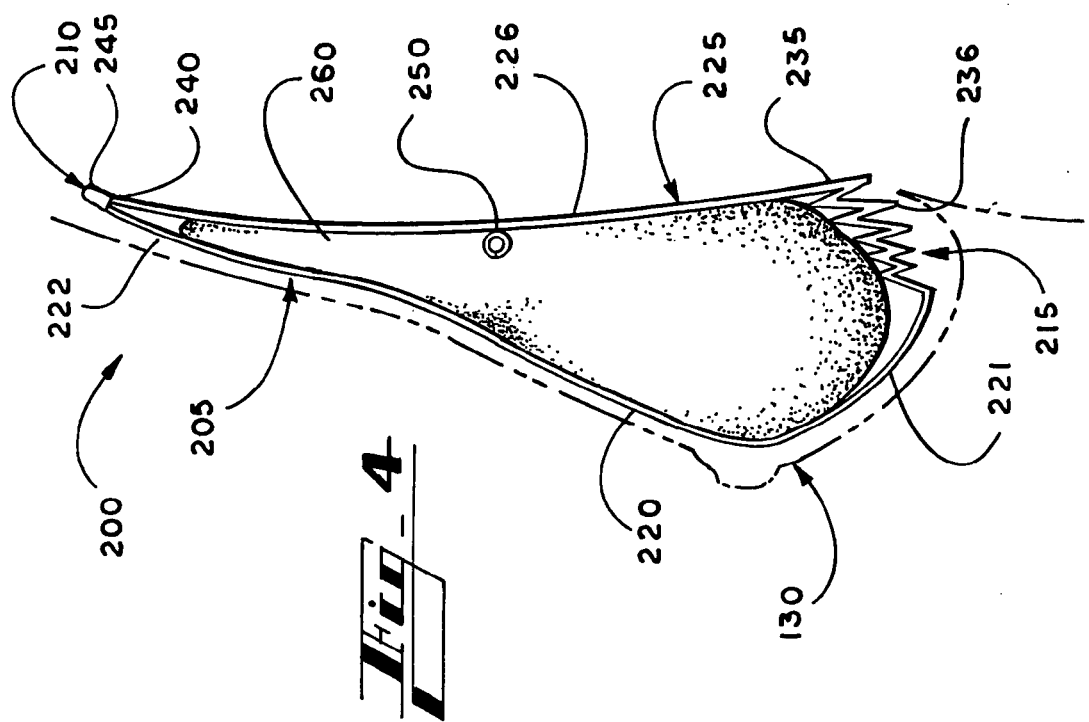
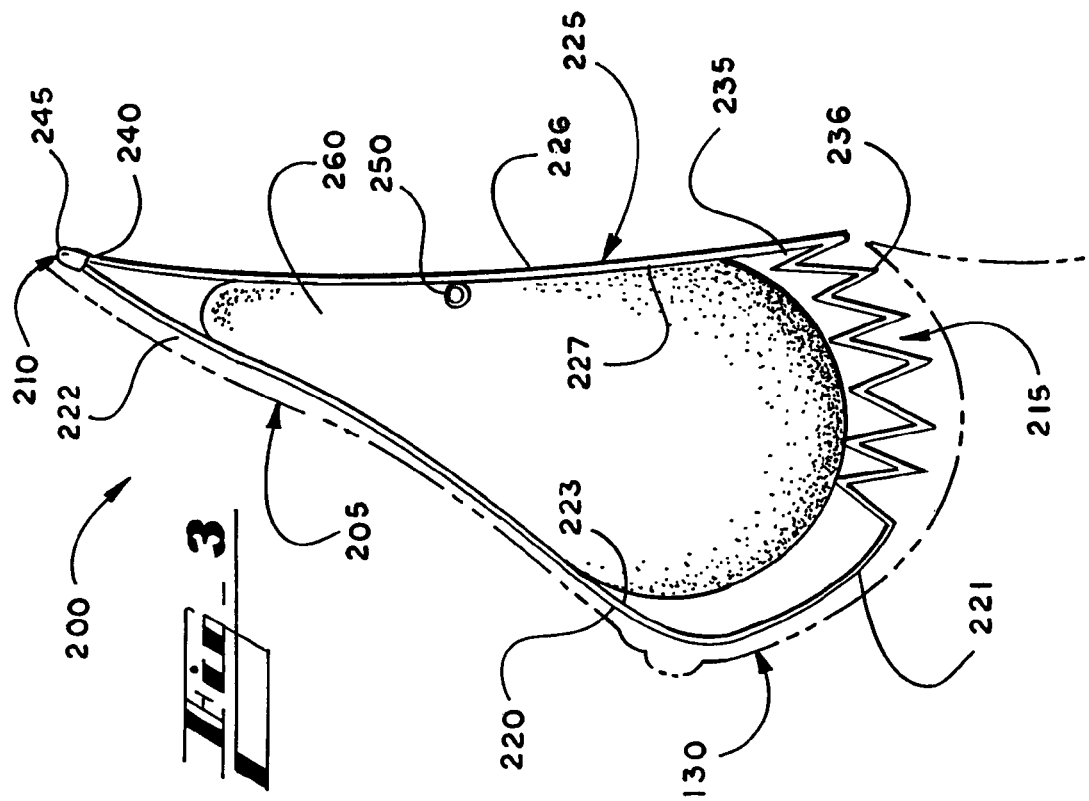

HINGING BREAST IMPLANT

BACKGROUND OF THE INVENTION

I. Field of the Invention

The present invention relates generally to the field of prosthesis and, more particularly, to a hinging breast implant with variable size.

II. Description of the Related Art

In general, modern breast implants do not allow the implant to be variably sized either during or after surgery. As such, people who desire to change the overall size and shape of their breasts must have major surgery if they desire to change the overall size and shape of their breast.

SUMMARY

In general, the invention features a hinging breast implant that includes an exterior shell and an inner bladder. The exterior shell is typically a bellows having a plurality of pleats so that the outer size of the implant is variable so that different sizes and shapes can be obtained. The rear of the housing closest to the patient's interior is typically shaped in order to conform to the patient's rib cage and internal connective tissues. Conversely, the front of the housing is shaped to naturally conform to the outer shape of the patient. Typically, the inner bladder can be filled with a suitable filling material, liquid, gas or solid. As the bladder is filled, the exterior shell expands in a manner that creates a lifting effect and a ballooning effect. An valve is connected to both the exterior shell and the inner bladder. The valve can be used to fill the bladder external to the patient without the need for further surgery after the implant is initially implanted into the patient. Local anesthetic can be used to access the appendage that is located close to the surface of the skin.

In general, in one aspect, the invention features a breast implant, including an external housing having a top end and a bottom end and a hollow interior, a bladder having an interior reservoir and located within the hollow interior of the housing, a valve connected to the bladder and protruding from the housing, a hinging mechanism connected to the top end of housing.

In one implementation, the housing includes a front panel having a generally rounded contour that mimics the outer contour of a human chest, a rear panel having a generally concave outer surface adapted to fit against the general shape of a human chest and a flexible and pleated wall connected between the front and rear panels.

In another implementation, the bladder is connected to an inner surface of the housing.

In another implementation, the bladder is connected to an inner surface of the rear panel.

In another implementation, a portion of the bladder is in mechanical contact with an inner surface of the front panel.

In another implementation, the implant further includes a compartment formed between a lower portion of the bladder and an internal portion of the pleated wall.

In still another implementation, a first end of the pleated wall is connected to one side of the hinging mechanism and a second end of the pleated wall is connected to an opposite side of the hinging mechanism.

In yet another implementation, the hinging mechanism is an elongated cap that encloses an end of the front and rear panels and a portion of the pleated wall.

In another implementation, the pleated wall forms a bellows.

In another implementation, the implant further includes a liquid filling the interior reservoir of the bladder.

In another implementation, the implant further includes a gas filling the interior reservoir of the bladder.

In another implementation, the implant further includes a solid filling the interior reservoir of the bladder.

In another implementation, the valve is adapted to remain external to the patient and adapted to receive a filler.

In another implementation, the filler is added and removed as needed to vary the size of the implant.

In another aspect, the invention features a breast implant, including an external housing having a top end and a bottom end and a hollow interior, a valve connected to the housing and a hinging mechanism connected to the top end of housing.

In one implementation, the housing includes a front panel having a generally rounded contour that mimics the outer contour of a human chest, a rear panel having a generally concave outer surface adapted to fit against the general shape of a human chest and a flexible and pleated wall forming a bellows connected between the front and rear panels.

In another implementation, the invention features a liquid filling the interior reservoir of the bladder.

In another implementation, the implant further includes a gas filling the interior reservoir of the bladder.

In another implementation, the implant includes a filler that can be added and removed through the valve to vary the overall size of the implant.

In another aspect, the invention features a breast implant, an external housing having a front panel, a rear panel, a top end and a bottom end and a hollow interior and means for variably inflating and resizing the external housing.

One advantage of the invention is that surgery is not required to change the overall size and shape of the implant once it is surgically implanted.

Another advantage of the invention is that the implant has the ability to hinge upward, creating a lifting effect.

Another advantage of the invention is that the implant has the ability to change the amount of lift and ballooning.

Another advantage of the invention is that the implant provides further stretching of the skin for those patients who need it, such as mastectomy patients, thereby providing a more natural tapered look that the surgeon does not have to construct with other tissue.

Other objects, advantages and capabilities of the invention will become apparent from the following description taken in conjunction with the accompanying drawings showing the preferred embodiment of the invention.

BRIEF DESCRIPTION OF THE DRAWINGS

FIG. 1 illustrates a side view of an embodiment of a hinging breast implant in a first state;

FIG. 2 illustrates a side view of the embodiment of the hinging breast implant of FIG. 1 in a second state;

FIG. 3 illustrates a side view another embodiment of a hinging breast implant in a first state; and FIG. 4 illustrates a side view of the embodiment of the hinging breast implant of FIG. 3 in a second state.

DETAILED DESCRIPTION

Referring to the drawings wherein like reference numerals designate corresponding parts throughout the several figures, reference is made first to FIG. 1 that illustrates a side view of an embodiment of a hinging breast implant 100 in a first state. In general, the implant 100 includes a flexible but semi-rigid external housing 105 having a top end 110, a bottom end 115 and a hollow interior. The housing 105 further includes a front panel 120 and a rear panel 125. The front panel 120 typically includes a generally rounded contour that mimics the outer contour of a human chest, and more specifically, the contour of a woman's breast 130. The front panel 120 can include a variety of shapes that can also be custom fit for a particular person's shape. Although the housing 105 is generally rigid, a variety of suitable materials can be used in the housing 105 and particularly the front panel to create a soft and natural firmness that mimics human tissue. The front panel 120 typically has a low end 121 that is generally larger than a high end 122 of the front panel 120. The front panel 120 is tapered from the low end 121 to the high end 122 in order to create a shape that mimics the breast 130. The rear panel 125 typically includes a generally concave outer surface 126 adapted to fit against the general shape of a human chest so that the rear panel 125 can fit properly against connective, muscular and skeletal tissue. In one implementation, the rear panel 125 can also be customized in order to more properly and naturally fit a particular person.

A flexible and pleated wall 135 is connected between the front panel 120 and rear panel 125. In general, the wall 135 includes several folds that form a number of pleats when the wall 135 is closed upon itself. The pleats allow the wall 135 to expand and contract as necessary. The outer edges 136 of the pleats are adapted to rest within the tissue of the person having the implant 100. This expansion and contracting as well as the overall construction of the implant 100 is similar to a bellows. In general, the wall has a folded upper edge 140 that is connected to a hinging mechanism 145. The hinging mechanism 145 can be an elongated cap that is secured to and covers the upper edge 140 of the pleated wall 135. In another implementation, the hinging mechanism 145 can be an elongated bar to which the upper edge 140 is connected, similar to a book binding. In this implementation, the elongated bar can include a slit into which the upper edge 140 connects. In another implementation, the hinging mechanism 145 is a clamp that applies clamping pressure to the upper edge 140 of the wall 135. In the implementations described above for the hinging mechanism 145, a first end of the wall 135 can generally be connected to one side of the hinging mechanism 145 and a second end of the wall 135 is connected to an opposite side of the hinging mechanism 145. In general, the hinging mechanism 145 is adapted to remain a fixed point so that the remaining portions of the housing 105 can lift and expand with respect to the hinging mechanism 145.

The implant 100 further includes a valve 150 connected to the housing 105. The valve 150 can typically include an elongated stem 155. The valve 150 can be located at various locations on the housing 105. In one implementation, the valve 150 is located on the pleated wall 135. The valve 150 is coupled to the hollow interior of the housing 105. The valve 150 can be any suitable type of valve that allows the implant 100 to be filled with a suitable gas, liquid or solid used to fill the implant. In general, the valve 150 is adapted to remain external to the patient after the implant 100 is surgically implanted into the patient. By remaining external, the valve 150 can be used to add and remove the filling gas, liquid or solid as needed or desired by the patient, without having to have any further surgery. Therefore, the valve 150 acts as a shunt that can eventually be removed and the connection to the housing 105 permanently sealed. In another implementation, the valve 150 can be located under the patient's skin, close to the surface. In this way, minor surgery can be performed to access the valve 150 to add or remove the filling gas, liquid or solid.

FIG. 1 illustrates the implant 100 in a first state that is semi-expanded. The flexible wall 135 is adapted to expand and contract as needed as the filling gas liquid or solid is added or removed, thereby allowing the implant 100 to by variably sized. As such, the implant 100 has a variable size that can be adjusted as the patient desires by adding or removing the gas, liquid or solid via the valve 150 after surgery. In general, the flexible nature of the implant causes a lifting effect and a ballooning effect when the filling gas, liquid or solid is added to the housing 105. The lifting effect of the implant 100 is generally enabled by the presence of the hinging mechanism 145. By having the fixed point at the hinging mechanism 145, the front panel 120 can lift, with the low end 121 experiencing the outward arc of the lift. The general flexibility of the wall 135 also allows the implant 100 to balloon, having an overall expansive effect and generally increasing the overall size of the implant 100. In another implementation, the pleated wall 135 can be replaced with a material that is suitable for expansion and contraction similar to expansion and contraction of latex or rubber.

FIG. 2 illustrates a side view of the embodiment of the hinging breast implant 100 of FIG. 1 in a second state. As described above, the implant 100 includes the flexible-but semi-rigid external housing 105 having the top end 110, the bottom end 115, the hollow interior, the front panel 120 and the rear panel 125. The front panel 120 typically includes a generally rounded contour that mimics the outer contour of a human chest. The front panel 120 typically has a low end 121 that is generally larger than a high end 122 of the front panel 120. The front panel 120 is tapered from the low end 121 to the high end 122 in order to create a shape that mimics the breast 130. The rear panel 125 typically includes a generally concave outer surface 126 adapted to fit against the general shape of a human chest so that the rear panel 125 can fit properly against connective, muscular and skeletal tissue.

The flexible and pleated wall 135 is connected between the front panel 120 and rear panel 125. In general, the wall 135 includes several folds that form a number of pleats when the wall 135 is closed upon itself. The pleats allow the wall 135 to expand and contract as necessary. The wall has a folded upper edge 140 that is connected to a hinging mechanism 145. The several implementations of the hinging mechanism 145 are described above. In general, the hinging mechanism 145 is adapted to remain a fixed point so that the remaining portions of the housing 105 can lift and expand with respect to the hinging mechanism 145.

The implant 100 further includes the valve 150 connected to the housing 105 and is coupled to the hollow interior of the housing 105. The valve 150 can be any suitable type of valve that allows the implant 100 to be filled with a suitable gas, liquid or solid used to fill the implant. surface.

FIG. 2 illustrates the implant 100 in a second state that is almost fully deflated. FIGS. 1 and 2 are shown in order to illustrate the expansive nature of the implant 100 due to the hinging and ballooning effects that are enables by the flexible wall 135 and the hinging mechanism 145. As described above, the flexible wall 135 is adapted to expand and contract as needed as the filling gas, liquid or solid is added or removed. As such, the implant 100 has a variable size that can be adjusted as the patient desires by adding or removing the gas, liquid or solid via the valve 150 after surgery. In general, the flexible nature of the implant causes a lifting effect and a ballooning effect when the filling gas, liquid or solid is added to the housing 105. In FIG. 2 much of the filling has been removed and therefore the implant 100 has decreases overall size in both outward appearance and overall volume. It is understood that even in this deflated state, the implant 100 still serves a prosthetic purpose showing an overall shape due to the front panel 120. In general, therefore, the implant 100 typically has an inherent minimum size due to the prosthetic nature of the front panel 120.

FIG. 3 illustrates a side view another embodiment of a hinging breast implant 200 in a first state. In general, the implant 200 includes a flexible but semi-rigid external housing 205 having a top end 210, a bottom end 215 and a hollow interior. The housing 205 further includes a front panel 220 and a rear panel 225. The front panel 220 typically includes a generally rounded contour that mimics the outer contour of a human chest, and more specifically, the contour of a woman's breast 130. The front panel 220 can include a variety of shapes that can also be custom fit for a particular person's shape. Although the housing 105 is generally rigid, a variety of suitable materials can be used in the housing 205 and particularly the front panel to create a soft and natural firmness that mimics human tissue. The front panel 220 typically has a low end 221 that is generally larger than a high end 222 of the front panel 220. The front panel 220 is tapered from the low end 221 to the high end 222 in order to create a shape that mimics the breast 130. The rear panel 225 typically includes a generally concave outer surface 226 adapted to fit against the general shape of a human chest so that the rear panel 225 can fit properly against connective, muscular and skeletal tissue. In one implementation, the rear panel 225 can also be customized in order to more properly and naturally fit a particular person.

A flexible and pleated wall 235, similar to the pleated wall 135 as described above with respect to FIGS. 1 and 2, is connected between the front panel 220 and rear panel 225. The wall 235 is shown generally in phantom to illustrate further features of the implant 200. In general, the wall 235 includes several folds that form a number of pleats when the wall 235 is closed upon itself. The pleats allow the wall 235 to expand and contract as necessary. The outer edges 236 of the pleats are adapted to rest within the tissue of the person having the implant 200. This expansion and contracting as well as the overall construction of the implant 200 is similar to a bellows. In general, the wall has a folded upper edge 240 that is connected to a hinging mechanism 245. The hinging mechanism 245 can be an elongated cap that is secured to and covers the upper edge 240 of the pleated wall 235. In another implementation, the hinging mechanism 245 can be an elongated bar to which the upper edge 240 is connected, similar to a book binding. In this implementation, the elongated bar can include a slit into which the upper edge 240 connects. In another implementation, the hinging mechanism 245 is a clamp that applies clamping pressure to the upper edge 240 of the wall 235. In the implementations described above for the hinging mechanism 245, a first end of the wall 235 can generally be connected to one side of the hinging mechanism 245 and a second end of the wall 235 is connected to an opposite side of the hinging mechanism 245. In general, the hinging mechanism 245 is adapted to remain a fixed point so that the remaining portions of the housing 205 can lift and expand with respect to the hinging mechanism 245.

The implant 200 further includes a bladder 260 located within the hollow interior of the housing 205. The bladder 200 is comprised of a material that can retain its general shape but expand and contract as a filling such as a gas liquid and solid is inserted into the bladder 260, similar to a balloon. In general, as described further below, the bladder 260 is adapted to expand and contract to cause a respective expansion and contraction of the housing 205. The bladder can be connected to an inner surface of the housing such as an inner surface 227 of the rear panel 225.

The implant 200 further includes a valve 250 connected through the housing 205 and connected to the bladder 260. The valve 250 is similar to the valve 150 described above with respect to FIGS. 1 and 2. However, there is no stem for illustrative purposes. The valve 250 can be located at various locations on the housing 205. In one implementation, the valve 250 is located on the pleated wall 235. The valve 250 can be any suitable type of valve that allows the implant 200 to be filled with a suitable gas, liquid ir solid used to fill the implant. Typically, the filler is forced through the valve 250 into the bladder which has an interior reservoir. In general, the valve 250 is adapted to remain external to the patient after the implant 200 is surgically implanted into the patient. By remaining external, the valve 250 can be used to add and remove the filling gas, liquid and solid as needed or desired by the patient, without having to have any further surgery. Therefore, the valve 250 acts as a shunt that can eventually be removed and the connection to the housing 205 permanently sealed. In another implementation, the valve 250 can be located under the patient's skin, close to the surface. In this way, minor surgery can be performed to access the valve 250 to add or remove the filling gas, liquid ir solid.

FIG. 3 illustrates the implant 200 in a first state that is semi-expanded. The flexible wall 235 is adapted to expand and contract as needed as the filling gas, liquid or solid is added or removed into or from the bladder 260 thereby allowing the implant 200 to be variably sized. As such, the implant 200 has a variable size that can be adjusted as the patient desires by adding or removing the gas, liquid or solid via the valve 150 after surgery. In general, the bladder 260 is adapted to expand and therefore push against inner surfaces of the housing 205 in order to expand the housing 205 as needed. Conversely, as the bladder contracts as the gas, liquid or solid filler is removed, the housing 205 also contracts. Connection to the inner surface 227 of the rear panel 225 helps to stabilize the bladder 260 within the housing 205 and to allow expansion outward against an inner surface of the wall 235 and an inner surface 223 of the front panel 220. By this connection to the inner surface 227 of the rear panel 225, greater degrees of freedom are generally enabled for the expansion and contraction. In general, expansion is not needed toward the chest. Therefore, as the bladder 260 expands and contracts, there is movement with respect to the front panel 220 and the wall 235. The bladder 260 is typically in some mechanical contact with the inner surfaces of the bladder 260. The flexible nature of the implant 200 causes a lifting effect and a ballooning effect when the filling gas, liquid or solid is added to the bladder 260. The lifting effect of the implant 200 is generally enabled by the presence of the hinging mechanism 245. By having the fixed point at the hinging mechanism 245, the front panel 220 can lift, with the low end 221 experiencing the outward arc of the lift. The general flexibility of the wall 235 also allows the implant 200 to balloon, having an overall expansive effect of the implant 200 and generally increasing the overall size of the implant 200. In another implementation, the pleated wall 235 can be replaced with a material that is suitable for expansion and contraction similar to expansion and contraction of latex or rubber. During the expansion and contraction, compartments such as compartment 270 can form within the hollow interior of the housing 205 when the bladder is in the semi-expanded or expanded state.

FIG. 4 illustrates a side view of the embodiment of the hinging breast implant 200 of FIG. 3 in a second state. As described above, the implant 200 includes the flexible but semi-rigid external housing 205 having the top end 210, the bottom end 215, the hollow interior, the front panel 220 and the rear panel 225. The front panel 220 typically includes the generally rounded contour that mimics the outer contour of a human chest and the low end 221 that is generally larger than the high end 222 of the front panel 220. The front panel 220 is tapered from the low end 221 to the high end 222 in order to create a shape that mimics the breast 130. The rear panel 225 typically includes a generally concave outer surface 226 adapted to fit against the general shape of a human chest so that the rear panel 225 can fit properly against connective, muscular and skeletal tissue.

The flexible and pleated wall 235 is connected between the front panel 220 and rear panel 225. In general, the wall 235 includes several folds that form a number of pleats when the wall 235 is closed upon itself. The pleats allow the wall 235 to expand and contract as necessary. In general, the wall has a folded upper edge 240 that is connected to a hinging mechanism 245. The embodiments of the hinging mechanism 245 are described above. In general, the hinging mechanism 245 is adapted to remain a fixed point so that the remaining portions of the housing 205 can lift and expand with respect to the hinging mechanism 245.

The implant 200 further includes a bladder 260 located within the hollow interior of the housing 205. The bladder 200 is comprised of a material that can retain its general shape but expand and contract as a filling such as a gas liquid and solid is inserted into the bladder 260, similar to a balloon. In general, as described further below, the bladder 260 is adapted to expand and contract to cause a respective expansion and contraction of the housing 205. The bladder can be connected to an inner surface of the housing such as an inner surface 227 of the rear panel 225.

The implant 200 further includes a valve 250 connected through the housing 205 and connected to the bladder 260. The valve 250 can be any suitable type of valve that allows the implant 200 to be filled with a suitable gas, liquid or solid used to fill the implant. Typically, the filler is forced through the valve 250 into the bladder 260 which has an interior reservoir.

FIG. 4 illustrates the implant 200 in a second state that is almost fully deflated. FIGS. 3 and 4 are shown in order to illustrate the expansive nature of the implant 200 due to the hinging and ballooning effects that are enabled by the flexible wall 135 and the hinging mechanism 145. As described above, the flexible wall 235 is adapted to expand and contract as needed as the filling gas, liquid or solid is added or removed. As such, the implant 200 has a variable size that can be adjusted as the patient desires by adding or removing the gas, liquid or solid via the valve 250 and into the bladder 260, after surgery. In general, the bladder 260 is adapted to expand and therefore push against inner surfaces of the housing 205 in order to expand the housing 205 as needed. Conversely, as the bladder contracts as the gas, liquid or solid filler is removed, the housing 205 also contracts. The flexible nature of the implant 200 causes a lifting effect and a ballooning effect when the filling gas, liquid or solid is added to the bladder 260 and thereby expanding against the housing 205. In FIG. 4 much of the filling has been removed and therefore the implant 200 has decreased overall size in both outward appearance and overall volume. It is understood that even in this deflated state, the implant 200 still serves a prosthetic purpose showing an overall shape due to the front panel 220. In general, therefore, the implant 200 typically has an inherent minimum size due to the prosthetic nature of the front panel 220.

As described above, the filler was generally referred to as a gas, liquid and solid. It is understood that several types of filler that can be used to vary the size of the variable sized hinging implants.

The foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A breast implant, comprising:
   an external housing having a top end and a bottom end, a hollow interior, a front panel having a generally rounded contour that mimics the outer contour of a human chest, a rear panel having a generally concave outer surface adapted to fit against the general shape of a human chest and a flexible and pleated wall connected between the front and rear panels;
   a bladder having an interior reservoir and located within the hollow interior of the housing;
   a valve connected to the bladder and protruding from the housing; and
   a hinging mechanism connected to the top end of housing, wherein a first end of the pleated wall is connected to one side of the hinging mechanism and a second end of the pleated wall is connected to an opposite side of the hinging mechanism.

2. The implant as claimed in claim 1 wherein the bladder is connected to an inner surface of the housing.

3. The implant as claimed in claim 2 wherein the bladder is connected to an inner surface of the rear panel.

4. The implant as claimed in claim 1 wherein a portion of the bladder is in mechanical contact with an inner surface of the front panel.

5. The implant as claimed in claim 1 further comprising a compartment formed between a lower portion of the bladder and an internal portion of the pleated wall.

6. The implant as claimed in claim 1 wherein the hinging mechanism is an elongated cap that encloses an end of the front and rear panels and a portion of the pleated wall.

7. The implant as claimed in claim 1 wherein the pleated wall forms a bellows.

8. The implant as claimed in claim 1 further comprising a liquid filling the interior reservoir of the bladder.

9. The implant as claimed in claim 1 further comprising a gas filling the interior reservoir of the bladder.

10. The implant as claimed in claim 1 further comprising a solid filling the interior reservoir of the bladder.

11. The implant as claimed in claim 1 wherein the valve is adapted to remain external to the patient and adapted to receive a filler.

12. The implant as claimed in claim 11 wherein the filler is added and removed as needed to vary the size of the implant.

13. A breast implant, comprising:
   an external housing having a top end and a bottom end and a hollow interior a front panel having a generally rounded contour that mimics the outer contour of a human chest a rear panel having a generally concave outer surface adapted to fit against the general shape of a human chest and a flexible and pleated wall connected between the front and rear panels;

a bladder formed as an integral part of the housing and having an interior reservoir;

a valve connected to the housing; and a hinging mechanism connected to the top end of housing, wherein a first end of the pleated wall is connected to one side of the hinging mechanism and a second end of the pleated wall is connected to an opposite side of the hinging mechanism.

* * * * *